US00PP22675P2

(12) United States Plant Patent
Egger

(10) Patent No.: US PP22,675 P2
(45) Date of Patent: Apr. 17, 2012

(54) *TIARELLA* PLANT NAMED 'APPALACHIAN TRAIL'

(50) Latin Name: ***Tiarella* spp.**
Varietal Denomination: Appalachian Trail

(75) Inventor: Janet Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 9 days.

(21) Appl. No.: 12/927,595

(22) Filed: Nov. 17, 2010

(51) Int. Cl.
*A01H 5/00* (2006.01)

(52) U.S. Cl. ..... Plt./486

(58) Field of Classification Search ..... Plt./486
See application file for complete search history.

*Primary Examiner* — Susan McCormick Ewoldt
(74) *Attorney, Agent, or Firm* — Jondle & Associates, P.C.

(57) ABSTRACT

A new and distinct cultivar of *Tiarella* plant characterized by medium large ovate leaves with prominent black splatter markings, medium large ovate leaves with prominent black splatter markings, excellent vigor, and an excellent trailing habit.

1 Drawing Sheet

Botanical denomination: *Tiarella* spp.
Variety designation: 'Appalachian Trail'.

BACKGROUND OF THE INVENTION

The present invention relates to a new and distinct cultivar of a hardy herbaceous perennial of the genus *Tiarella,* and known by the cultivar name 'Appalachian Trail'. The genus *Tiarella* is a member of the family Saxifragaceae.

The new cultivar originated from a planned breeding program as a cross between *Tiarella* 'Running Tapestry', an unpatented plant, as the seed parent and massed proprietary trailing *Tiarella* as the pollen parent. The exact pollen parent is unknown. Compared to the seed parent, *Tiarella* 'Running Tapestry', the new cultivar is more trailing and better marked. Compared to *Tiarella* 'Delaware', U.S. Plant Pat. No. 21,980, the new cultivar is better marked and better trailing.

SUMMARY OF THE INVENTION

This plant is characterized by the following:

1. medium large ovate leaves with prominent black splatter markings;
2. an excellent trailing habit; and
3. excellent vigor.

The new variety has been reproduced only by asexual propagation (division and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the foliage and flowers of a 6 month old *Tiarella* 'Appalachian Trail' grown in a 4" pot in a cool greenhouse in Canby, Oreg.

FIG. 2 shows a 10 month old plant grown in a 10" container.

DETAILED PLANT DESCRIPTION

The following is a detailed description of the new *Tiarella* cultivar based on observations of one-year-old plants grown together in one gallon containers in a cool greenhouse in March in Canby, Oreg. Canby is Zone 8 on the USDA Hardiness map. Temperatures range from a high of 95 degrees F. in August to an average low of 32 degrees F. in January. Normal rainfall in Canby is 42.8 inches per year. The color descriptions are all based on The Royal Horticultural Society Colour Chart, 5$^{th}$ edition.

Plant:
- *Type.*—Herbaceous perennial.
- *Hardiness.*—USDA Zones 4 to 9.
- *Form.*—Trailing.
- *Size.*—65 cm wide and 8.5 cm high from the soil to the top of the foliage.
- *Vigor.*—Excellent.
- *Roots.*—Fibrous, freely branching, fine, and white in color; roots develop easily from stem cuttings.

Stem:
- *Type.*—Decumbent with adventitious roots at the nodes.
- *Size.*—Grows to 2 mm wide and 47 cm long.
- *Surface.*—Pubescent.
- *Internodes.*—2 cm to 8 cm long.
- *Color.*—Yellow Green 148B in low light and Brown 200D in high light.

Basal leaves:
- *Type.*—Simple.
- *Arrangement.*—Rosette.
- *Shape.*—Ovate.
- *Lobing.*—Variable, 3 to 7 shallow lobes, terminal lobe the longest.
- *Margins.*—Crenate.
- *Venation.*—Palmate.
- *Apex.*—Acute.
- *Base.*—Cordate, overlapping.
- *Blade.*—Grows to 8 cm long and 7 cm wide.
- *Surface.*—Hispid top and bottom, matte.
- *Petiole description.*—5 to 10 cm and 1.5 mm wide, hirsute, Yellow Green 148B in low light and Brown 200D in high light.

*Leaf color.*—Topside, Green 137A with a dark splatter pattern along the veins, Greyed Purple 187A darkening to N186A on older leaves; bottom side Yellow Green 147C with markings Greyed Purple N187A.

Stem leaves:

*Type.*—Simple.
*Arrangement.*—Alternate.
*Shape.*—Ovate.
*Lobing.*—Variable, 0 to 3 very shallow lobes.
*Margins.*—Crenate.
*Venation.*—Palmate.
*Apex.*—Mucronulate.
*Base.*—Cordate, sometimes overlapping.
*Blade.*—Grows to 4 cm long and 3.2 cm wide.
*Surface.*—Hispid top and bottom, matte.
*Petiole description.*—1.5 to 3 cm long and 1.5 mm wide, hirsute, Yellow Green 148B in low light and Brown 200D in high light.
*Leaf color.*—Topside, Green 137A with a slight dark splatter pattern along the veins, Greyed Purple 187A darkening to N187A on older leaves topside, Green 137A with a dark splatter pattern along the veins, Greyed Purple 187A darkening to N186A on older leaves; bottom side Yellow Green 147C with markings Greyed Purple N187A.

Inflorescence:

*Type.*—Raceme.
*Flower number.*—30 to 45 per raceme.
*Size of inflorescences.*—Grows to 8.5 cm long and 2.5 cm wide.
*Number of inflorescences.*—3 to 8 in first spring flush.
*Bloom period.*—March to mid June in Canby, Oreg.
*Peduncle.*—Unbranched, grows to 27 cm long and 2.5 mm wide at the base, hispid, Yellow Green 146B.
*Pedicel.*—8 mm long, hispid, Yellow Green 147C.
*Lastingness.*—A raceme blooms for about 3 weeks.

Flower bud:

*Size.*—3 mm deep and 2.5 mm wide.
*Description.*—Ovoid, down facing until open.
*Surface.*—Glandular.
*Color.*—White N155C.

Flower:

*Type.*—Perfect, actinomorphic, sepals petaloid.
*Shape.*—Rotate.
*Flower size.*—8 mm wide and 5 mm deep including stamens and pistil.
*Corolla.*—5 petals, each 3 mm long and 1 mm wide, lanceolate with a clawed base, margin entire, tip acuminate, glabrous on both sides, White NN155C inside and outside.
*Calyx.*—8 mm wide, 5 sepals, backs glandular, inside glabrous, petaloid, parted almost to the base; lobes obovate, tips obtuse, margins entire, 3 mm long and 1.5 mm wide, White NN155C with tips Yellow Green 147C inside and out.
*Stamens.*—10, conspicuously exerted; filaments 4 mm long, White NN155D; anthers undehisced Red 39B; pollen Orange Red 32A.
*Pistil.*—1, White 155C, 5 mm long, ovary 2 mm long, glandular.
*Fragrance.*—None.

Fruit and seed: 6 mm long and 2.5 mm wide, Yellow Green 146C with little seed set; seed Brown 200A, oval, 1.5 mm long.

Pest and disease resistance: This new hybrid shows good mildew tolerance, the main problem for *Tiarella*. No major pest problems. It is susceptible to root weevils, like all *Tiarella*.

I claim:

1. A new and distinct cultivar of *Tiarella* plant herein illustrated and described.

* * * * *

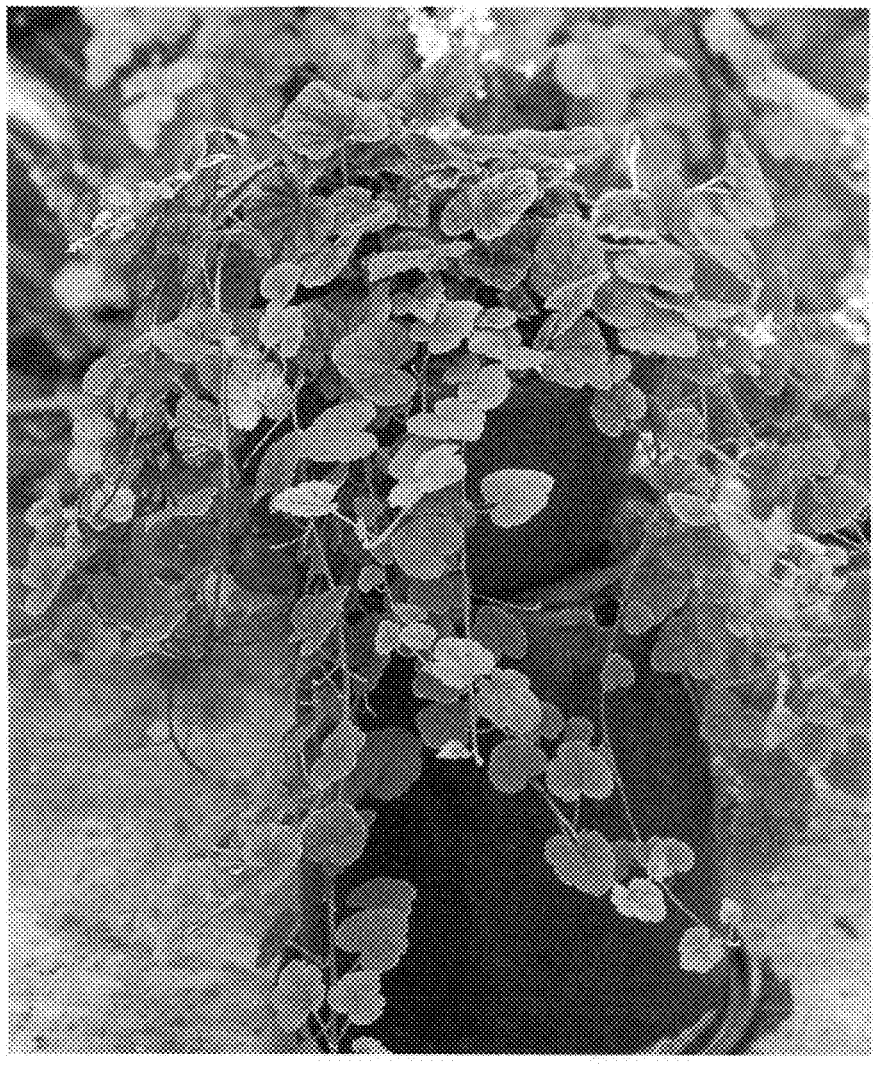

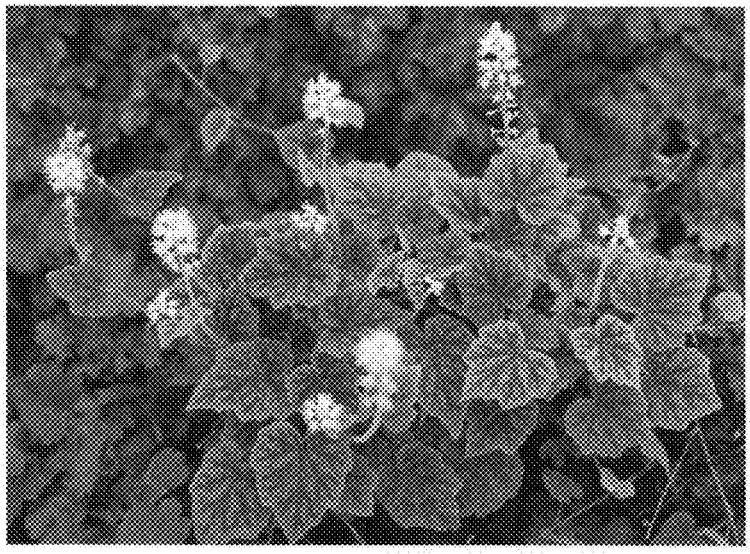
Figure 1 above
Figure 2 below